(12) United States Patent
Zahid et al.

(10) Patent No.: US 11,109,888 B1
(45) Date of Patent: Sep. 7, 2021

(54) TISSUE GRAFT SPLITTER

(71) Applicant: King Abdulaziz University, Jeddah (SA)

(72) Inventors: Talal Mansoor H. Zahid, Jeddah (SA); Abdulhameed F. Alkhateeb, Jeddah (SA); Mohammed Nadershah, Jeddah (SA); Emad Ali Khan, Jeddah (SA); Zuhair Saleh Natto, Jeddah (SA); Sana Ghazi Alttas, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/987,932

(22) Filed: Aug. 7, 2020

(51) Int. Cl.
| | |
|---|---|
| *A61B 17/322* | (2006.01) |
| *B26D 3/28* | (2006.01) |
| *B26D 7/04* | (2006.01) |
| *A61B 17/32* | (2006.01) |
| *A61B 17/00* | (2006.01) |
| *B26D 1/00* | (2006.01) |
| *B26D 1/06* | (2006.01) |
| *A61B 17/14* | (2006.01) |

(52) U.S. Cl.
CPC ............ *A61B 17/322* (2013.01); *B26D 3/28* (2013.01); *B26D 7/04* (2013.01); *A61B 17/147* (2016.11); *A61B 2017/0015* (2013.01); *A61B 2017/00075* (2013.01); *A61B 2017/00761* (2013.01); *A61B 2017/00792* (2013.01); *A61B 2017/00969* (2013.01); *A61B 2017/3225* (2013.01); *A61B 2017/320064* (2013.01); *B26D 1/065* (2013.01); *B26D 2001/004* (2013.01)

(58) Field of Classification Search
CPC ............ Y10S 83/9155; Y10T 83/0281; Y10T 83/0267; Y10T 83/5669; Y10T 83/7487; Y10T 83/758; Y10T 83/821; A61B 17/322; A61B 17/147; A61B 2017/00075; A61B 2017/0015; A61B 2017/00761; A61B 2017/00792; A61B 201/00969; A61B 2017/320064; A61B 2017/3225; B26D 1/065; B26D 2001/004; B26D 3/28; B26D 7/04; B26D 7/02; B26D 7/025

See application file for complete search history.

(56) References Cited

U.S. PATENT DOCUMENTS

| | | | | |
|---|---|---|---|---|
| 4,184,472 A | * | 1/1980 | Benedicto | ................ B26D 3/28 125/23.01 |
| 6,418,826 B1 | * | 7/2002 | Suzuki | ..................... A24B 3/06 83/111 |
| 9,594,004 B2 | * | 3/2017 | Fry | ......................... B26F 3/004 |

FOREIGN PATENT DOCUMENTS

| | | |
|---|---|---|
| CN | 203622477 U | 6/2014 |
| CN | 207768527 U | 8/2018 |
| CN | 209027824 U | 6/2019 |

OTHER PUBLICATIONS

Foulad, et al. ; Practical Device for Precise Cutting of Costal Cartilage Grafts to Uniform Thickness ; Arch Facial Plast Surg/vol. 13(No. 4) ; Jul./Aug. 2011 ; 7 Pages.

* cited by examiner

*Primary Examiner* — Phong H Nguyen
(74) *Attorney, Agent, or Firm* — Oblon, McClelland, Maier & Neustadt, L.L.P.

(57) ABSTRACT

A tissue splitting device for splitting a harvested soft tissue to provide a layer of tissue having a uniform thickness and methods for tissue transplantation using uniform layers of tissue.

20 Claims, 4 Drawing Sheets

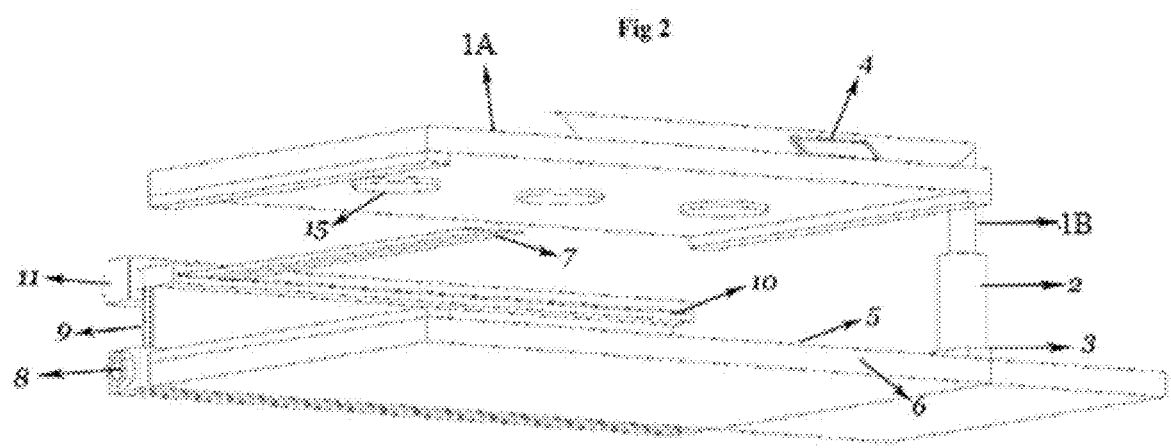
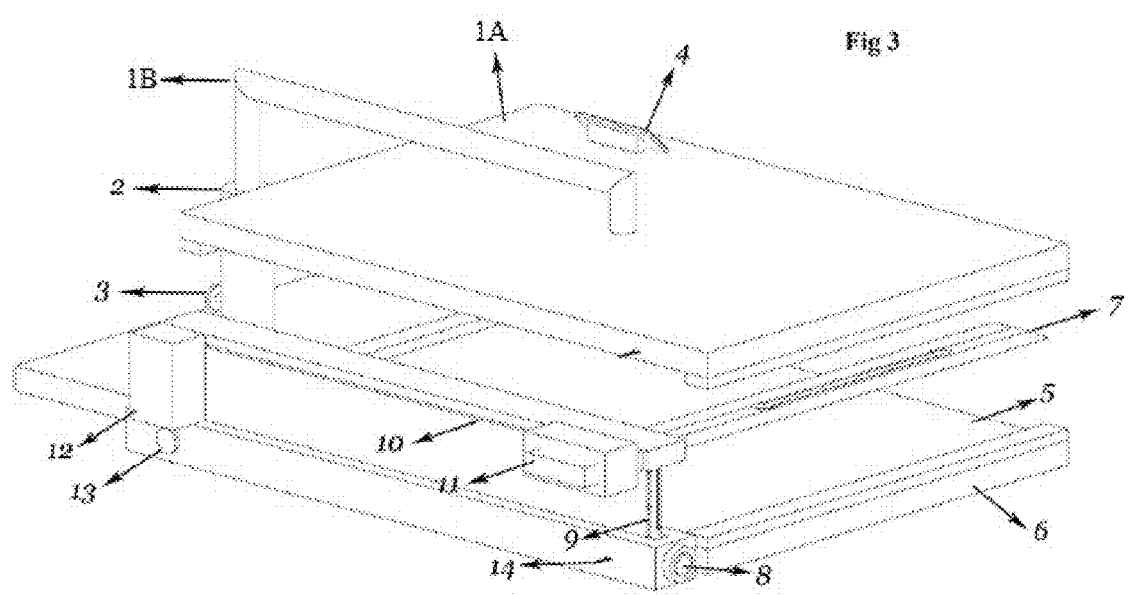

TISSUE GRAFT SPLITTER

BACKGROUND OF THE INVENTION

Field of Invention

The present invention relates to the field of reconstructive surgery and particularly to a tissue splitting device that produces viable, undamaged and uniformly sized soft tissue layers for transplantation.

Description of Related Art

Soft tissue grafts are commonly used in reconstructive surgery including for gingival, dermal, and cartilage grafting and sometimes for bone grafting. Traditionally a surgeon manually trims a harvested tissue to prepare a graft having a desired size and thickness for implantation at a grafting site; Rijhwani et al., *Free Gingival Autograft and Subepithelial Connective Tissue Graft for the Treatment of Gingival Recession: A Brief Review and Report of Three Cases.* Seema Yadav Journal of Contemporary Dentistry, September-December 2016; 6(3):225-232; Harris R J. *Creeping attachment associated with the connective tissue with partial-thickness double pedicle graft.* J. Periodontol. 1997 September; 68(9):890-9.

Soft tissue grafts include gingival grafts which are commonly made within the oral cavity. Such grafts include free gingival grafts, connective tissue grafts, and pedicle grafts. An oral graft is often a strip of tissue which is obtained most commonly from an intraoral donor site such as the hard palate.

Such grafts are often necessary to treat gum recession, cover the exposed root, increase tissue thickness to provide or enhance keratinized tissue, or to treat gum or tooth sensitivity; Rijhwani et al, 2016, supra. Gum recession occurs when the teeth roots become exposed. There are several reasons for gum recession which include gum disease, trauma, aging, over brushing, and poor tooth position; Dembowska E, et al., *Subepithelial connective tissue graft in the treatment of multiple gingival recession.* Oral Surg Oral Med Oral Pathol Oral Radiol Endod. 2007 September; 104(3):e1-7. Epub 2007 Jul. 6; Rijhwani et al, 2016, supra; Wang L, et al., *Refinement and Evaluation of Modified Minimally Invasive Harvest Technique for Subepithelial Connective Tissue.* J Craniofac Surg. 2018 July; 29(5):1287-1290. Gum recession and tooth exposure often result in a patient having uncomfortable sensations when eating hot, cold foods, or when the teeth are exposed to air. Gum recession is also associated with a higher risk of caries and with an unaesthetic appearance and often leads to a diminished self-image.

Besides oral grafts, soft-tissue grafts have been used to reconstruct the anterior cruciate ligament with hamstring or fascia lata (deep fascia of the thigh) grafts within the femoral tunnel in the knee joint which is a common area of tearing of these ligaments in sports activities such as football or skiing; Wilde J, et al., *Revision anterior cruciate ligament reconstruction.* Sports Health. 2014 November; 6(6):504-18.

There are several ways to obtain a tissue graft. Tissue, such as connective tissue from the palate, to be used as a connective tissue graft may be harvested using the trap-door technique described by Edel, A. *Clinical evaluation of free connective tissue grafts used to increase the width of keratinized gingiva.* J Clin Periodontol 1974; 1:185-96. Another method is the parallel incision method developed and described by Langer B and Langer L. *Subepithelial connective tissue graft technique for root coverage.* J. Periodontol. 1985; 56:715-20. Other methods include those modified by Harris who provided a new method using a scalpel with two blades mounted 1.5 mm apart; Harris R. J., *The connective tissue and partial thickness double pedicle graft: A predictable method of obtaining root coverage.* J. Periodontol. 1992; 63:477-86; by Raetzke who introduced the two crescent-shaped horizontal incisions to obtain graft; tissue; Raetzke P B. *Covering localized areas of root exposure employing the "Envelope" technique.* J. Periodontol. 1985; 56:397-402; by Bruno used the two horizontal incisions only; Bruno J F. *Connective tissue graft technique assuring wide coverage.* Int. J. Periodontics Restorative Dent. 1994; 14:127-37; and by Hurzeler who used a single incision technique which has several advantages such as the primary healing at the donor site and very slight postoperative pain and complications; Hurzeler M B, Weng D. *A single incision technique to harvest subepithelial connective tissue grafts from palate.* Int J Periodontics Restorative Dent. 1999; 19:279-87—each incorporated herein by reference in its entirety.

Typically palatial connective tissue is harvested using a blade oriented perpendicular to the palatal tissue surface. A single incision is then made to the bone through a horizontal direction approximately 2 to 3 mm apical to the gingival margin of the maxilla.

The length of the incision is determined by the size of the graft required to cover the proposed area, as well as depth for the elevation and removal of the donor tissue. A partial-thickness dissection is then made within the single incision, leaving an adequate thickness of the palatal flap intact to minimize the chance of sloughing of the overlying tissue; Goldstein M, et al., *A critical evaluation of methods for root coverage.* Crit Rev Oral Biol Med. 1996; 7(1):87-98.

The dissection is carried out as far apical as necessary to obtain the desired dimensions of the graft. The connective tissue with underlying periosteum is then carefully dissected from the palate with the elevator. A primary closure using sutures is recommended. A free gingival graft (FGG) is harvested manually through horizontal incisions that are made in the two interdental papillae adjacent to the area to be grafted; Butler B L. *The subepithelial connective tissue graft with a vestibular releasing incision.* J. Periodontol. 2003 June; 74(6):893-8; Camargo P M, et al. *The use of free gingival grafts for aesthetic purposes.* Periodontol 2000. 2001; 27:72-96—both incorporated herein by reference.

The incisions are made at right-angles to the gingival surface, creating a clear butt-joint design. Two vertical apically diverging incisions are then placed at each end of the horizontal incision and extended beyond the mucogingival junction. Using sharp dissection of the scalpel blade, a split-thickness flap is elevated beyond the apical end of the vertical incisions, taking care that alveolar bone should not be exposed.

A FGG of 1.5 mm-1.5 cm thickness is then harvested from the hard palate from between the distal area of canine to the mid-palatal of first molar, with the dimension of the gingival graft being one and a half times the dimensions of the recipient area. After that, the fatty layer is removed on a side table. This requires stabilization of the graft on a wooden tongue blade or using a small instrument. The surgeon then usually uses a small blade to shave the epithelial and fat layer.

Grafts from the donor sites can be obtained from two areas of interest: the anterior palate which has a large surface or the posterior part of the palate, mainly the maxillary tuberosity and lateral palate. The maxillary tuberosity is very voluminous and thus a good site to harvest graft tissue; Zucchelli G, et al., *Patient morbidity and root coverage outcome after subepithelial connective tissue and deep epithelialized grafts: a comparative randomized-controlled clinical trial*. J Clin Periodontol. 2010b Aug. 1; 37(8):728-38; Zucchelli G, et al., *Predetermination of root coverage*. J Periodontol. 2010a July; 81(7):1019-26—both incorporated by reference. Grafts from this site are considered a good option for ridge augmentation while grafts from the lateral palate are good options for recession coverage. Both of these types of grafts are dense and firmer than those from the anterior palate and are unlikely to undergo significant post-operative shrinkage. However, such grafts have a higher chance for necrosis than anterior palate.

Soft tissue grafting, using tissue harvested from palatial, oral and other soft tissue surfaces, is complicated by the variability of thickness of freshly harvested graft-source tissue and by uneven tissue surfaces, such as corrugated palatal surfaces.

Moreover, often a surgically desired graft thickness is only a fraction of a millimeter and this can lead to surgical errors in during manual graft surgeries especially in soft tissue grafting. Moreover, adjustments to a tissue graft often result in wasting part of the graft and/or damaging the graft. Attempts have been made to improve graft harvesting and sizing methods such as by use of a mucotome or mucous membrane cutter; Gunay H, et al. *Harvesting technique using a mucotome and modified surgical procedure for root coverage with enamel matrix derivatives with and without a connective tissue graft*. Int J Periodontics Restorative Dent. 2008 October; 28(5):497-507; Grant, U.S. Pat. No. 4,240, 432A. Many such devices require freezing or embedding a tissue and are unsuitable for preparation of slices, sections or layers of viable tissue suitable for transplanting. Microtomes require lengthy procedures including embedding the tissue in paraffin wax or freezing the tissue. These procedures affect the viability of the living tissue and render it non-usable for tissue grafting. Moreover, the thickness of tissue provided by microtomes, which ranges from 30-500 µm for live tissue and 10-500 µm for fixed tissue, is not suitable or practical for tissue grafting or suturing. Such prior attempts do not provide a solution for effectively splitting the graft after harvesting it. Moreover, the corrugated surface of the palate presents a challenge in achieving a uniform thickness desirable for many tissue grafts. Accordingly, these instruments still fail to overcome problems of obtaining viable, surgically desired soft tissue grafts having a substantially uniform thickness suitable for grafting procedures.

SUMMARY OF INVENTION

One aspect of the invention is a manual or automated tissue-graft splitter that maximizes utilization of a harvested graft tissue and which provides a viable graft having a uniform thickness. The device does not require that tissue be embedded prior to cutting, but can be described as a free-floating cutter that splits viable tissue. Moreover, it can measure the thickness of a tissue and set a cutting location to produce a split tissue of a desired thickness.

The tissue-splitting device or apparatus disclosed herein provides a number of advantages to surgeons or dentists whose practices involve tissue grafting. The device quickly, easily, and accurately provides viable grafts of uniform thickness for uses in surgical procedures, especially in dental surgery. The device can be adjusted to provide grafts of different thicknesses and compared to manual procedures can provide a standardized, viable graft of a desired thickness when used by different practitioners.

Another aspect of the invention is a surgical method of grafting soft tissues, especially gingival tissues, using graft sections or layers of soft tissue produced using the tissue graft splitter.

A more complete appreciation of the disclosure and many of the attendant advantages thereof will be readily obtained as the same becomes better understood by reference to the following detailed description when considered in connection with the accompanying drawings below.

BRIEF DESCRIPTION OF THE DRAWINGS

FIG. 2 illustrates an embodiment with horizontal blade 7 positioned between upper plate 1 and lower mounting plate 6. The bottom surface of upper plate 1A is equipped with three pressure sensors 15 which measure an amount of pressure imposed on a soft tissue sample sandwiched between the upper plate 1 and lower rough surface 5 of the lower mounting plate 6. The pressure value imposed on a soft tissue sample is measured by sensors 15 and transmitted to display 4. Thickness control knob 8 and height scale indicator 9 are used to set the thickness of a tissue between rough surface 5 of the lower mounting plate and blade 7. Cutting blade motor 11 is used to power cutting blade 7.

FIG. 3 shows a motor-side view of the tissue splitting device. Upper plate 1 and display 4 are shown along with the height adjustment 2 and upper plate height adjustment control 3. Blade/saw movement motor 12 (or manual control 12) and blade/saw movement control knob 13 (or handle 13) move cutting blade motor 11 along horizontal blade channel 10. Height scale indicator 9 indicates the distance between the rough surface 5 of lower mounting plate 6 and horizontal blade 7. A connection or port for control cables from a microcontroller is shown at 14.

DETAILED DESCRIPTION OF THE INVENTION

Figure 1A:
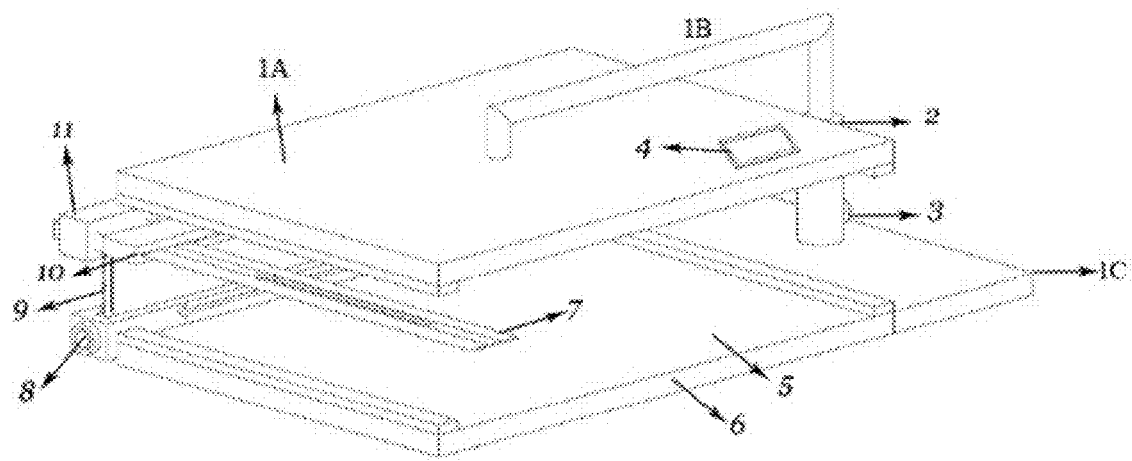
FIG. 1A depicts an embodiment of the tissue splitter having a horizontal cutting blade 7 interposed between an upper plate 1A and lower mounting plate 6. The height of upper plate 1A is adjusted by moving the adjustable arm 1B, which supports the upper plate 1A, up or down within height adjuster 2 using control knob 3. The height adjuster 2, adjustable arm 1B and upper plate 1A are anchored on base 1C. A display 4 is attached to the upper, external surface of plate 1A. Control knob 8 controls the distance between the upper plate 1A and lower mounting plate 6, a distance which can be quantified using height scale indicator 9. Lower mounting plate 6 has a rough top surface 5 for holding harvested soft tissue in place.

A tissue splitting device is disclosed which may be operated manually or automatically and which securely holds harvested tissue, especially soft tissue such as gingival tissue, during cutting so as to reproducibly provide layers of tissue having substantially uniform thicknesses. This tissue slices or layers produced by this device are viable, of substantially uniform thickness, and can be tailored using the device for particular surgical graft sites. Preferably the device and method work without requirement for embedment of the tissue during cutting and preferably provide adjustable sample thickness.

Embodiments of this technology include, but are not limited to the following.

One embodiment of the invention is a tissue splitting device comprising a clamp comprising a horizontal and parallel upper plate and lower mounting plate, and a horizontal space between the upper plate and lower mounting plate that can accommodate a harvested tissue, wherein a blade is horizontally positioned within the space between the upper plate and lower mounting plate and is operatively connected at one end to a blade movement channel that is horizontally aligned with the horizontal space between the upper plate and lower mounting plate, wherein a top surface of the upper plate comprises a display operatively connected to one or more pressure sensors on a bottom surface of the upper plate, and wherein a top surface of the lower mounting plate is a rough, frictioned surface that prevents tissue, such as slippery soft tissue placed in the clamp from sliding.

In some embodiments, the upper and lower plates are rectangular and approximately 10 to 30 cm long, 10 to 30 cm wide and 0.5 to 2 cm thick. The overall height of the device may range from about 5 to 20 cm. The width of a space between the upper and lower plates will depend on the type and volume of harvested tissue to be sliced or split, for example, it may range from about 0.25 to 3 cm. The dimensions of the plates can be adjusted when needed for a particular use, such as use in conjunction with clinical procedures requiring a larger tissue dimensions. In a preferred embodiment, the dimensions of the plates are about 10×10 cm and the adjustable arm is about 10 cm. In some embodiments, the adjustable arm may swivel sideways for easy placement of tissue. The other elements of the device will be proportionately sized based on the dimensions of the plates and adjustable arm.

In some embodiments, this tissue splitting or slicing device comprises an adjustable arm attached to support base and to the upper plate which can be raised to increase the height of the upper plate thereby increasing the height of the horizontal space between the upper and lower arms. The support base may be a flat, immobile surface or an anchor that firmly or immovably supports the arm and upper plate. In some embodiments, the lower plate rests on, or is attached to, the support base. Typically, the lower plate is fixed, while the upper plate is movable so as to control the height of the space between the two plates.

In other embodiments, it comprises an adjustable arm attached to the upper plate which can be raised to increase the height of the upper plate and wherein the adjustable arm is anchored to the lower mounting plate. Preferably, the lower mounting plate of the device is secured to, or rests on, a flat, immobile, horizontal surface. In some embodiments, the bottom surface of the upper plate is also a rough surface that prevents tissue placed in the clamp from sliding so that harvested tissue is secured both the rough surfaces of the upper and lower plates. In some embodiments, the bottom surface of the upper plate and/or the top surface of the lower mounting plate have a coefficient of friction on one or more tissues ranging from <0.5, 0.5, 0.6, 0.7, 0.8, 0.9, 1.0, 1.1, 1.2, 1.3 1.4, 1.5 to >1.5. In other embodiments, these surfaces may have a surface roughness Ra ranging from 0.5, 1, 2, 3, 4, 5, 10, 20, 50, 100 or ≥500 µm to 10, 20, 50, or 100 µm.

Preferably, a coefficient of friction between the plates and the tissue is at least 0.2, 0.3, 0.4, 0.5, or 0.6 to avoid slippage of soft tissue and a preferred roughness is about 1.1, 1.2, 1.3, 1.4, or 1.5 µm or more, when the coefficient friction is at least 0.4. Coefficients of friction and roughness may be determined by methods known in the art such as those described by Özin, M. C., Sümer, B., & Koç, I. M. (2018). *Estimation of Friction Force in Minimally Invasive Surgery with Tactile Sensors*. Academic Perspective Procedia, 1(1), 959-967; Shacham et al., J Biomech Eng. August 2010, 132(8). 084502, Rashid et al., Journal of the Mechanical Behavior of Biomedical Materials, Volume 14, October 2012, Pages 163-171, and Zhou, et al., (2015). Influence of surface roughness on the friction property of textured surface. *Advances in Mechanical Engineering, 7*(2), 1687814014568500 which are incorporated by reference. The plates may comprise polysulfone platens (substrates) of varying roughness between <0.12, 0.12. 0.5, 1, 2, 3, 4, 5, 6, 7 8 and >8 µm. A low roughness of 0.12 µm may be attained by polishing. Treatment with glass beads produces a mildly rough surface (roughness=1.3 µm) while 80-grit sandpaper produces a highly rough surface (roughness=8 µm). When lubricated human cartilage tissue was placed in contact with these three platens of increasing roughness, the coefficient of kinetic friction increased with roughness from 0.2 to 0.5 to 0.8; see Nguyen, Q. T., et al. (2010). *Macroscopic assessment of cartilage shear: effects of counter-surface rough-*

*ness, synovial fluid lubricant, and compression offset.* Journal of Biomechanics, 43(9), 1787-1793, incorporated by reference.

In some embodiments, a nonslip surface may be produced by attaching an abrasive such as sandpaper to a surface substrate or by using a surface substrate made of a polymeric material which provides control over roughness. Sandpaper increases the roughness and thus the coefficient of friction. For example, polysulfone platens (substrates) of varying roughness are described by Nguyen et al., id. Ballotini glass beads (Potters Industry, Malvern, Pa.) were used to increase the roughness of polysulfone to 1.3 µm and 80-grit sandpaper was used to get a highly rough surface (roughness=8 µm). A substrate surface comprising stainless steel, aluminum or another non-corrosive metal can be textured using an abrasive such as sandpaper. For example, 150-grit sandpaper increased the surface roughness of steel to 0.4-0.5 µm. Surface roughness can be further increased by using lower grit sandpaper.

In some embodiments of the tissue splitting device, the splitting device is sterile, especially those components or surfaces that come into contact with harvested or split tissue, such as the surfaces of upper and lower plates and the blade.

In some embodiments, the upper and lower plates, or their operative surfaces, may be replaceable. In others the upper and lower plates and blades can be cleaned, sterilized and/or reused. Similarly, the device may contain a blade that can be cleaned and sterilized or can use a replaceable blade.

In some embodiments, the blade has a straight or linear edge which extends lengthwise perpendicular to the direction of splitting or slicing a tissue. In other embodiments, the cutting blade may be circular and rotate during cutting or splitting a harvested tissue. In still other embodiments, a thin wire or beam, such as a laser beam, which extends lengthwise perpendicular to the direction of splitting or slicing a tissue may be used to slice tissue instead of a blade.

The blade, wire, or beam may be operated and moved manually to split the tissue or by a motor to which it is operatively connected. Typically, for an automated device, the device contains a motor that moves the blade along a blade movement channel parallel to the horizontal space between the upper and lower plates holding the harvested tissue. In embodiments, where the blade, wire or beam is moved manually, the blade, wire or beam may have a handle to provide for manual movement of the blade.

The height of the blade within the space between the upper and lower plates holding harvested tissue can be controlled by a blade height control and/or may contain a height scale indicator. In some embodiments, the height scale indicator will have visible scale markings that indicate the thickness of each piece of a split tissue. In other embodiments, the height scale indicator may be linked to a microcontroller and display which indicate the thickness of each piece of a split harvested tissue.

Figure 1B:
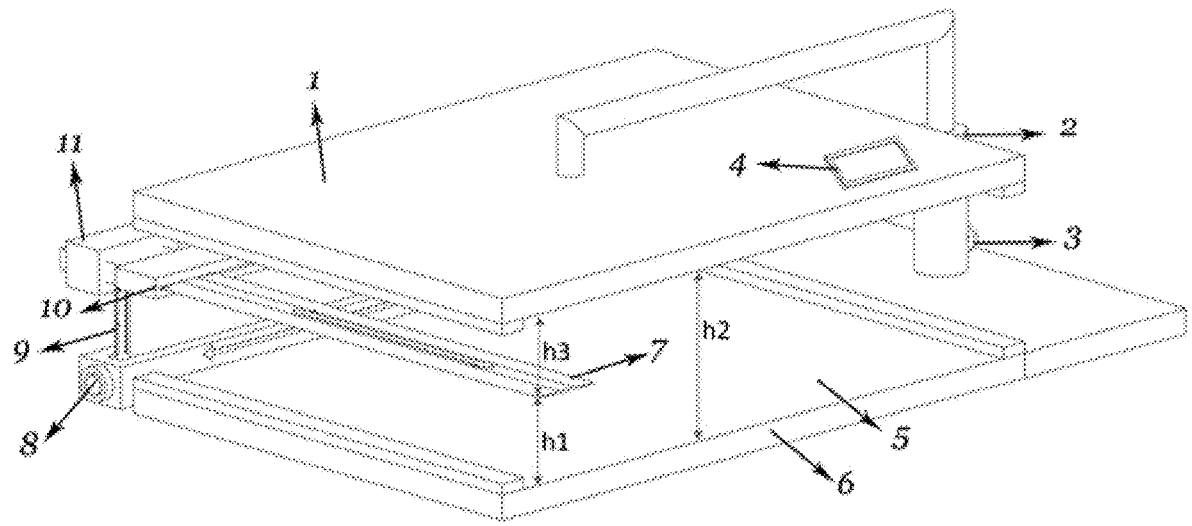
FIG. 1B depicts heights h1, h2 and h3, where h2 is the thickness of original tissue before cutting; h1 is the thickness of the intended tissue to be used after cutting, and h3=h2−h1 is the thickness of the remaining tissue after cutting and removing the intended tissue.

As shown by FIG. 1B, the thickness knob (3) measures the total thickness of the sample, (9) measures the height of the blade from the lower plate. Accordingly, the thickness of both pieces of the split tissue can be measured and calculated as shown by FIG. 1B. The lower plate upper surface where the tissue will rest (5) is used as a reference with height=zero. The total thickness of the original sample (h2) is determined by the reading on the tissue thickness control knob (3) and can be displayed on the LCD screen. The thickness of the new sample after cutting is (h1) which is the height of the blade from the lower plate surface (5). The thickness of the remaining tissue is calculated as the difference between (h2) and (h1).

Typically, the blade height is set at a predetermined value during splitting or slicing of the harvested tissue to provide a slice or layer or tissue having a uniform thickness. In another embodiment, the blade height may be varied during cutting so as to provide a resulting slice or layer of tissue with two or more sections having different thicknesses or a layer of tissues with tapered ends.

The splitting device may further comprise one or more controllers or microprocessors operatively connected to a pressure sensor, pressure sensor display, adjustable arm, blade motor, and/or motor that moves the blade along the blade channel. Displays for each of these elements may optionally be connected to the element and to a microcontroller. For example, the microcontroller can control an amount of pressure placed on harvested tissue in the device before, during or after the tissue is cut by the blade by adjusting the height of adjustable arm 1B, adjust the horizontal progression of the blade through the tissue, and/or the sawing speed of the cutting blade.

Another embodiment of the invention involves a method for tailoring or splitting a soft tissue comprising harvesting a tissue sample comprising a soft tissue, securing the harvested soft tissue between the upper and lower plates of the device as disclosed herein, setting the horizontal blade, wire or beam to a preselected position (or to one or more sequential preselected positions), and horizontally cutting the secured soft tissue sample, and recovering a slice of the soft tissue having the preselected thickness. There is no need to freeze, fix, or embed a harvested tissue in embedding agent like wax or resin. A harvested tissue sample is kept viable and free during the splitting or cutting process.

In another embodiment, a harvested tissue may be sliced two, three or more times to provide several slices or layers of uniform or preselected thickness. These multiple layers may be taken from the top or bottom of a harvested tissue or from the center of a harvested tissue secured between the upper and lower plates.

Once a layer or slice of tissue is split or sliced from the harvested tissue, it may be removed from the device, washed with a sterile saline, antibiotic-containing, or a nutritive medium, and, if necessary, have its dimensions, such as length and width, further tailored to fit a particular graft site. A layer or slice of tissue may be retained or refrigerated prior to use as a graft, for example, at a temperature about 0, 10, 20, 25, 30 to 37° C.

In some embodiments the soft tissue that is split is connective tissue, keratinized gingival tissue, non-keratinized gingival tissue, a soft tissue comprising a mucous membrane, epithelium, or endothelial or cardiac tissue. Keratinized gingival tissue derives from keratinized gingiva which is the part of the oral mucosa which covers the gingiva and hard palate. It extends from the free gingival margin to the mucogingival junction and consists of the free gingiva as well as the attached gingiva. It can be transplanted to restore defects or areas of recession or degeneration in keratinized gingiva. Non-keratinized gingival tissue derives from alveolar mucosa which is non keratinized oral epithelium and is located apical to the keratinized tissue, delineated by the mucogingival junction (MGJ). Such mucosa can surround a healthy tooth and thus when transplanted may be used to replace or restore tissue around a tooth.

Preferably, the splitting device as disclosed herein is oriented as shown in the figures with the lower plate supported by or fixed to horizontal surface with the blade cutting the tissue between the upper and lower plates horizontally, end-to-end. In other embodiments, the entire device may be rotated so that the blade cuts the tissue vertically upward or vertically downward or at an angle.

Another embodiment of the invention is a method for performing a soft tissue transplant comprising surgically removing a soft tissue from a subject, splitting the soft tissue in the splitting device as disclosed herein under conditions that provide a layer of viable soft tissue of uniform or preselected thickness (or thicknesses), and transplanting the layer of tissue into a graft site on a subject. In some embodiments, this method uses a soft tissue that is gingival or connective tissue and provides layers of uniform thickness for transplantation into the mount of a subject who is in need of a connective tissue or free gingival tissue.

Soft Tissue.

The term soft tissue refers to tissues that connect, support, or surround other structures and organs of the body, not being bone. Soft tissue includes tendons, ligaments, fascia, skin, fibrous tissues, fat, and synovial membranes, and muscles, nerves and blood vessels. All tissues found within the body that are not those of bones or certain organs are considered soft tissues. In some embodiments, the composition of soft tissue comprises mainly of elastin and collagen and it may comprise fibroblasts, chondroblasts or other cells that produce elastin or collagen. Ground substance, non-cellular, fibrous components of a cell, also can make up part of a soft tissue.

Many soft tissues are hyperelastic materials, which have a nonlinear stress-strain curve, and have the potential to undergo large deformations and still return to the initial configuration when unloaded. A soft tissue may be viscoelastic, incompressible or anisotropic. Some viscoelastic properties observable in some soft tissues are relaxation, creep and hysteresis. Mechanical properties of soft tissues may be measured using various methods including hyperelastic macroscopic models based on strain energy, mathematical fits where nonlinear constitutive equations are used, and structurally based models where the response of a linear elastic material is modified by its geometric characteristics.

Other tissues that may be split using the device disclosed herein soft tissues such as skin layers, mucus membrane, connective tissue, epithelium, cardiac tissue, keratinized gingival, non-keratinized, gingival, para-keratinized, gingival, cartilage, cornea, periosteum, muscles, vessels, artery, membrane and barrier tissue.

The porcine soft tissue system is representative of the human system in terms of tissue mechanics; Shacham et al., supra. The liver is among the 'softer' soft tissues in the body and can help decide a reasonable compressive stress/pressure limit to prevent tissue damage in the experiments. Based on a study by Chen et al., the porcine liver starts showing significant changes in microarchitecture, such as an increase in the density of fissure cracks, within 30% compressive strain. Looking at the stress-strain curve for this tissue, keeping the pressure under 30 kPa is important to prevent tissue damage. Since the liver is softer than most other soft tissues, this threshold should work for other tissues too.

Moreover, biomechanical engineering studies may be conducted for each tissue by the end-user to measure tissue pressure injury tolerance and biomechanics of oral mucosa. The results can them be fed into the microprocessor to determine the safe pressure parameters and the user can choose which the tissue and preset pressures will be utilized. However, manual override for the pressure can be done by the user by selecting a value in bar or pascal.

Soft tissue grafts that may be produced using the device as disclosed herein include gum tissue grafts such as connective tissue grafts and free gingival grafts. Connective tissue grafting is a common method used to treat root exposure. During the procedure, a flap of skin is cut at the roof of the mouth (palate) and tissue from under the flap, called subepithelial connective tissue, is removed and then stitched to the gum tissue surrounding the exposed root. After the connective tissue forming the graft has been removed from under the palatal flap, the flap is stitched back down. A free gingival graft is similar to a connective-tissue graft and involves the use of tissue from the roof of the mouth. However, instead of making a flap and removing tissue under the top layer of flesh, a small amount of tissue is removed directly from the roof of the mouth and then attached to the gum area being treated. This method is used most often in people who have thin gums to begin with and need additional tissue to enlarge the gums. For either type of graft, the harvested tissue may be sliced to a uniform thickness or may otherwise be tailored as disclosed herein. A tissue or layer of split or sliced tissue having a substantially uniform thickness may vary in average thickness over its length by 1, 2, 5, 10, 15 or 20%. Preferably uniformity of the thickness should be within ±0.02, 0.03, 0.04, 0.05, 0.06, 0.07, 0.08, 0.09, or 0.1 mm.

Preferably, the device and splitting method as disclosed herein is configured to use, or involves soft tissue samples. However, in some embodiments, tissues other than soft tissues may be used, such as bone or a tissue of an organ, or tissue that is a mixture of soft and non-soft tissues. The device and method herein may be used to slice tissue harvested in vivo or ex vivo, tissue from a living or deceased donor, tissue from a tissue bank, tissues grown in vitro, or artificial tissue or biomaterials.

Surgical Blades.

The thickness and type of blade is typically selected based on the type of harvested tissue, the type of graft being made and the intended usage of the resulting sliced tissue. In some embodiments, the device uses a sharp steel, carbon-steel, glass, ceramic, sapphire, or diamond blade. A blade with a straight edge or a toothed blade may be selected depending on the type of harvested tissue and the thickness of the sliced layer to be cut. In some embodiments, a blade will have an antifriction coating, such as, but not limited to, platinum or polytetrafluoroethylene (RIFE) in preferred embodiments, the blade will act as a saw with back and forth motion or vibration for a linear blade and rotary motion for a circular blade. An interchangeable blade edge type is selected depending on the type of tissue.

Pressure Sensors.

Typically, thin or ultrathin compressive or shear stress sensors are attached to, or embedded in the bottom surface of the upper plate, so as to measure compressive force of the upper and lower plates on the tissue, or shear forces applied by the blade on a tissue sample secured between the upper and lower plates. These include ultrathin, embeddable sensors such as those described by hypertext transfer protocol secure://www.tekscan.com/products-solutions/embedded-force-sensors (incorporated by reference, last accessed Apr. 15, 2020). A pressure sensor may be configured to monitor compressive pressure or stress applied on a sample prior to or during splitting as well as a rate of change of compressive stress or pressure during handling or splitting. In some embodiments a sensor will detect and measure compressive stress between 0, 100, 200, 300, 400 or 500 psi. Such pressure sensors prevent crushing of a harvested tissue placed in the device by keeping pressure with a suitable range for a particular type of tissue. The pressure sensors can also be used to control pressure imposed on the harvested tissue to help stabilize it during cutting, or to flatten a tissue to a uniform thickness for splitting or cutting with the blade. Pressure sensors are preferably operably connected to a control for the adjustable arm and to a microcontroller that can maintain pressure within a preselected range by adjusting the height of the upper plate and which can display pressure values or harvested tissue thickness prior to and during cutting.

In some embodiments, in addition to compression pressure sensors, one or more sensors that measure mechanical resistance during cutting of a harvested tissue may be operatively connected to the cutting blade and horizontal movement motor. These can, for example, measure resistance imposed against the advancing cutting blade when a harvested tissue contains tissues of different densities. If desired, a microcontroller or circuit breaker mechanism may be used to auto-stop the blade when a change in mechanical resistance is detected which may indicate contact of the cutting blade with a material having a different or unexpected density.

Piezoelectric pressure sensors are well-suited to measure pressure in the near 30 kPa range as well as measuring mid-range pressures (100-108 Pa) and are incorporated by reference to Ripka, P., & Tipek, A. (Eds.). (2007). *Modern sensors handbook* (pp. 978-1). London, UK: ISTE. These sensors work on the principle of piezoelectricity, whereby the pressure signals are converted to electric signals in the form of voltage changes. They are less expensive; compact, and allow for dynamic pressure measurements with a response time on the order of a millisecond. Specifications for commercially available piezoelectric pressure sensors are incorporated by reference and include 0.7 kPa to 70 Mpa (worldwide web .avnet.com/wps/portal/abacus/solutions/technologies/sensors/pressure-sensors/core-technologies/piezoelectric/); and 0-108 Pa (worldwide web.bdsensors.de/en/pressure/piezoelectric-pressure-sensors/). Each of the above last accessed Jul. 27, 2020.

A 5 N load cell, which can measure forces as low as 20 mN, which is within the limits of what soft tissues are capable of handling can also be used and are incorporated by reference to Comley, K., & Fleck, N. (2012). *The compressive response of porcine adipose tissue from low to high strain rate*. International Journal of Impact Engineering, 46, 1-10. There are also 100 N load cells that have a resolution of 5 mN; Chen et al., supra. These can also be used to measure stresses (pressure) in the realm of soft tissue mechanics. A load cell can be placed under the lower substrate and force measured by it can be converted into pressure depending on the area of the sample.

Sensors will measure both compressive pressure and stress and strain forces. The stress and strain forces (measured from the plates) in combination with the compressive pressure data as well as blade movement sensor data, will control the splitting, action to avoid losing the viability of the tissue while maintaining the cutting efficiency.

Moreover, an autostop feature will be implemented through the software of the microprocessor whereby it will sense the amount of current drawn by the blade motor. If there is a change in the amount of current being drawn this will mean that the blade is cutting into a different tissue (different tissue density) and immediately the blade will be stopped Non-Slip Surface.

A non-slip, frictioned surface helps hold a harvested tissue on the bottom plate of the splitting device described herein. This surface may be imprinted with, or constitute a grating comprising a raised pattern of dots, ridges or other designs to provide a nonslip surface. Alternatively the top surface of the bottom plate may be treated with a commercially available non-slip coating, such as a nonslip or antislip paint or polymer (e.g. urethane or rubber) coating. In some embodiments, either or both of the bottom surface of the top plate and/or the top surface of the bottom plate may comprise nonslip or antislip surface. In some embodiments, the nonslip surface may have a raised edge at one or both ends or a depression into which a base of the harvested tissue may be placed to help secure the tissue during splitting.

Controller.

Sensors are operative connected to a controller, such as a microprocessor, that processes sensor input and outputs a pressure value on a display which is preferably attached to the top of the upper plate. In some embodiments, the controller may be operatively connected to a control that adjusts the splitting or rotational speed of the blade, to a control that adjusts the speed of blade along a blade movement channel through the tissue to modulate shear force on the tissue or to a control which adjusts the position of the upper plate so as to modulate the compressive pressure on the tissue. According to some embodiments, the controller can comprise one or more types of processors and/or electronic circuitry that can implement one or more computer and/or machine readable, writable, and/or executable components and/or instructions that can be stored in a memory. For example, the controller can perform various operations that can be specified by a computer and/or machine readable, writable, and/or executable components and/or instructions including, but not limited to, logic, control, input/output (I/O), arithmetic, and/or the like. In some embodiments, controller can comprise one or more central processing unit, multi-core processor, microprocessor, dual microprocessors, microcontroller, System on a Chip (SOC), array processor, vector processor, and/or another type of processor.

Thickness of slices. Tissue slices may range in thickness from about 0.1 (100 microns), 0.2, 0.3, 0.4, 0.5, 0.6, 0.7, 0.8, 0.9, 1, 2, 3, 4, 5, 6, 7, 8, 9, 10 or >10 mm or any intermediate value or subrange within this range. A desired slice thickness may be set using a thickness control knob to adjust blade height and/or by adjusting the height of the arm supporting the upper plate.

Pressure Range.

An amount of pressure applied on a tissue placed between the upper and lower plates of the device disclosed herein is selected so as to minimize damage to the tissue while securing it in the device so it can be uniformly sliced along its length. Preferably the amount of compressive force or shear pressure applied to the tissue during splitting does not decrease the viability of a graft made using the sliced tissue by more than 1, 2, 5, 10, 20, 30, 40 or 50% compared to a graft made using an originally harvested tissue or tissue slices prepared without mechanical application of compressive force. Pressure applied may preferably range from 50, 60, 70, 80, 90, 100, 110, 120, 120, 130, 140, 150 to 200 psi.

Typically, a compression range should be under 30 kPa to be safe in order to prevent tissue damage. Since information on human soft tissue damage mechanics is sparse, we will have to rely on the porcine system, which is considered to be quite representative of the human system in terms of tissue mechanics (Shacham et al., supra). Liver is among the 'softer' soft tissues in the body and can help decide a reasonable compressive stress/pressure limit to prevent tissue damage in the experiments. BasPorcine liver starts showing significant changes in microarchitecture, such as an increase in the density of fissure cracks, within 30% compressive strain; see Chen, J., et al. (2018). *Quantitative analysis of tissue damage evolution in porcine liver with interrupted mechanical testing under tension, compression, and shear*. Journal of Biomechanical Engineering, 140(7); Miller, et al. (2005). *Method of testing very soft biological tissues in compression*. Journal of biomechanics, 38(1), 153-158; and, Miller et al, (2002). *Mechanical properties of brain tissue in tension*. Journal of Biomechanics, 35(4), 483-490, and Bilston, L. E., et al. (2001). *Large strain behaviour of brain tissue in shear: some experimental data and differential constitutive model*. Biorheology, 38(4), 335-345, each incorporated by reference.

Looking at the stress-strain curve for this tissue, keeping the pressure under 30 kPa is important to prevent tissue damage. Since liver is softer than most other soft tissues, this threshold should work for other tissues too.

As shown in FIGS. 1A to 6, the device comprises a lower mounting plate 6 on which harvested tissue is placed for later splitting. It has a non-smooth or rough surface 5 to help harvested tissue to stay in place and not slip during splitting.

An upper plate 1A is lowered onto the tissue to keep it in place as well as keep its surface uniform. The upper plate height is controlled manually, electrically, electronically or by any other means using the tissue thickness control knob 3. The height control mechanism is housed in the upper plate height-adjustment cylinder 2.

Figure 4:
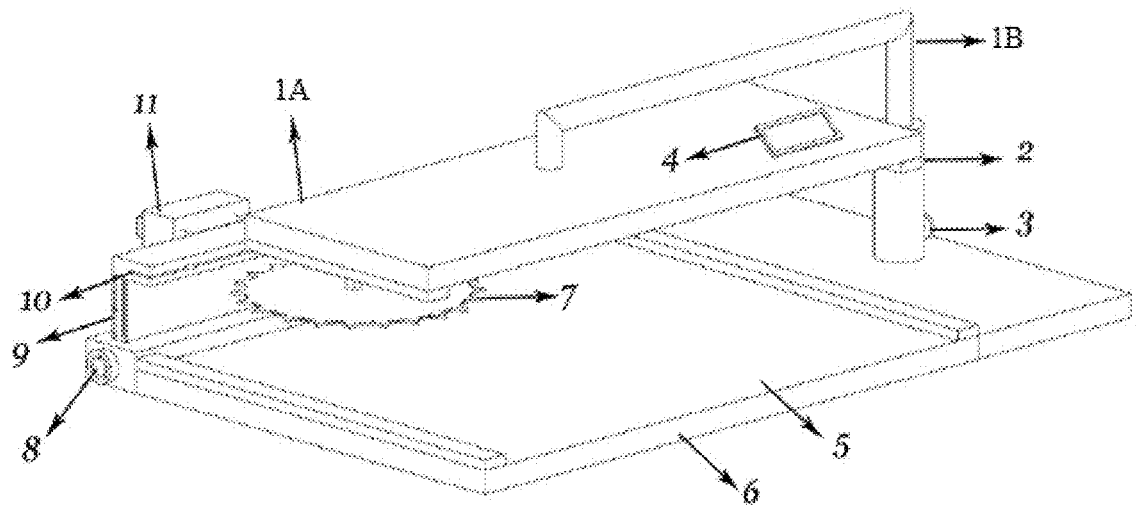
FIG. 4 shows an embodiment having a circular rotary saw blade 7 positioned between the rough surface 5 of lower mounting plate 6 and upper plate having a pressure indicator display 4. The height of upper plate 1 can be adjusted using height adjustment 2 and height adjustment control 3. Thickness control knob 8 and height scale indicator 9 are used to set the thickness of a tissue between rough surface 5 of the lower mounting plate and blade 7. Horizontal blade movement channel 10 and cutting blade motor 11 are shown at left.
Figure 5:
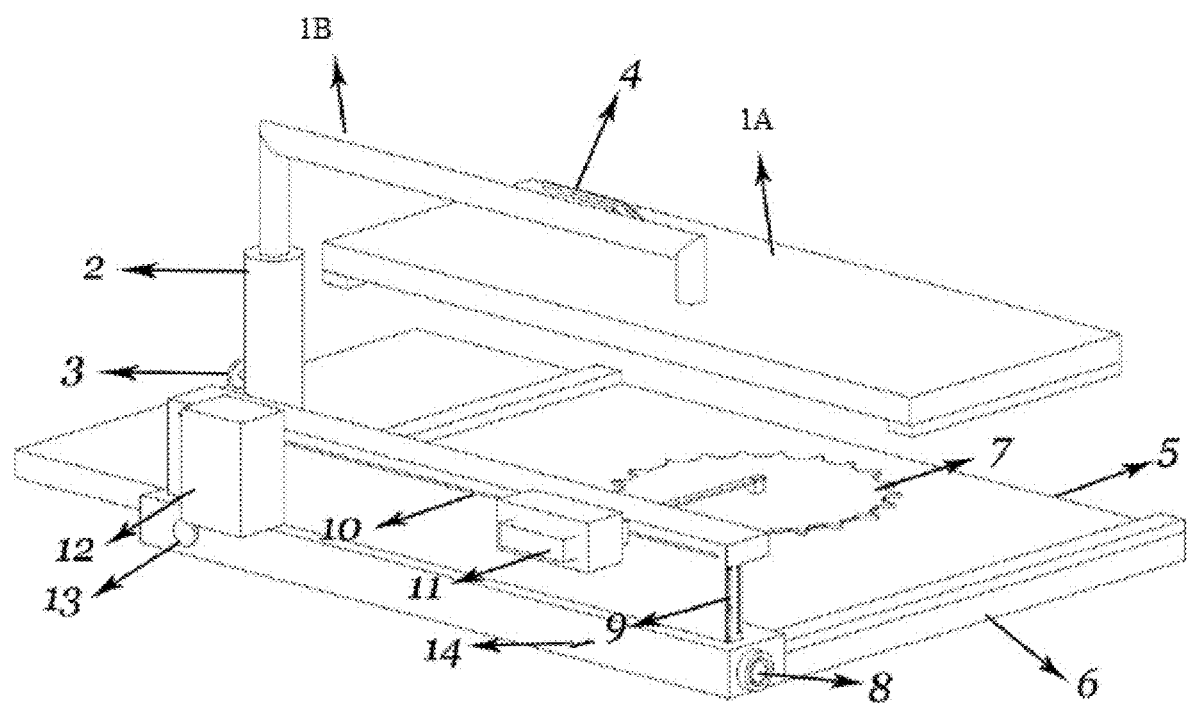
FIG. 5 depicts a motor-side view of an embodiment having a circular rotary saw blade 7 positioned between the rough surface 5 of lower mounting plate 6 and upper plate having a pressure indicator display 4. The height of upper plate 1A can be adjusted via arm 1B using extendible height adjustment 2 and height adjustment control 3. Thickness control knob 8 and height scale indicator 9 are used to set the height of the blade and thus the thickness of the resulting slices or layers of soft tissue obtained by cutting harvested tissue secured between rough surface 5 of the lower mounting plate and the upper plate 1A. Horizontal blade movement channel 10 and cutting blade motor 11 and blade horizontal movement motor 12 and blade movement control knob or handle 13 are shown in foreground. A connection or port for control cables from a microcontroller is shown at 14.
Figure 6:
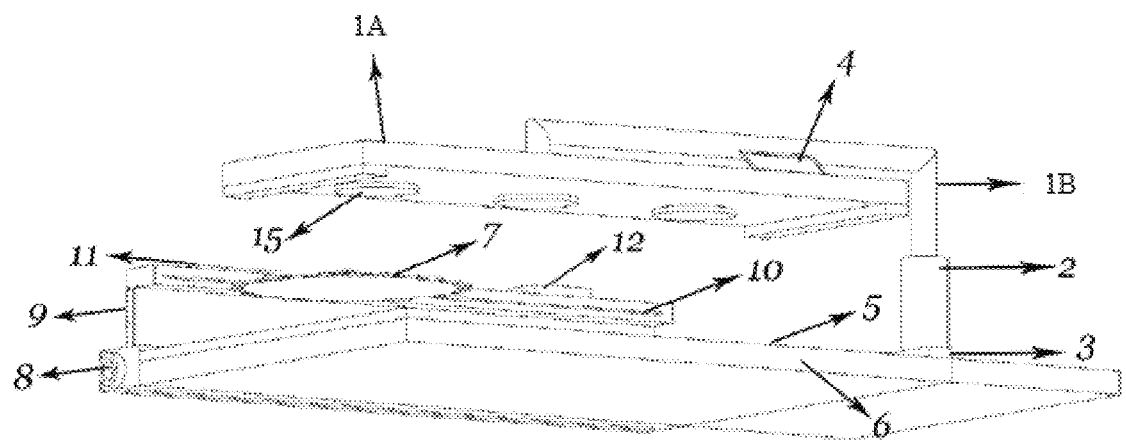
FIG. 6 provides a view of a device having a circular rotary blade 7, positioned between upper plate 1A having a pressure indicator 4 and rough surface 5 of lower plate 6, having three pressure sensors 15 on its lower, internal side. The height of upper plate 1A is adjustable using extendible/retractable height adjustment 2 and height adjustment control 3. Horizontal blade/saw movement channel 10, cutting blade motor 11, and blade horizontal motor 12 are depicted in background. Thickness control knob 8 and height scale indicator 9 are shown at left.

A pressure sensor 15 measures the pressure exerted by the upper plate 1 on the tissue and displays this pressure on the LCD screen 4. The user will exert the predetermined amount of pressure on the tissue sample so that it stays in place but does not exceed the pressure limit so as not to damage the tissue. A cutting device 7 which can be a horizontal blade shown in FIG. 1, 2, 3, or a rotating disc as shown in FIG. 4, 5, 6 or any other cutting mechanism, such as laser, a fine wire, is held by an arm 10 attached to the lower plate and can move in the horizontal blade movement channel 10 parallel to the length of the tissue sample between the plates.

The thickness of the tissue to be produced is determined by setting a cutting blade height which can be controlled manually, electrically, electronically or by any other means using the tissue thickness control knob 8. To provide a uniform and standardized thickness of a tissue slice or layer, this control knob may be calibrated to move in increments, for example in 0.1, 0.2, 0.3, 0.4, or 0.5 mm increments. A height scale indicator 9 is used to determine or quantify the thickness of the slice or layer of tissue removed from the harvested tissue.

The horizontal movement motor 12 is controlled by the cutting blade movement control 13 which may be operably connected to a microcontroller. The sawing speed of a blade may be controlled via cutting blade motor 11 which may be operably connected to a microcontroller.

Figure 7:
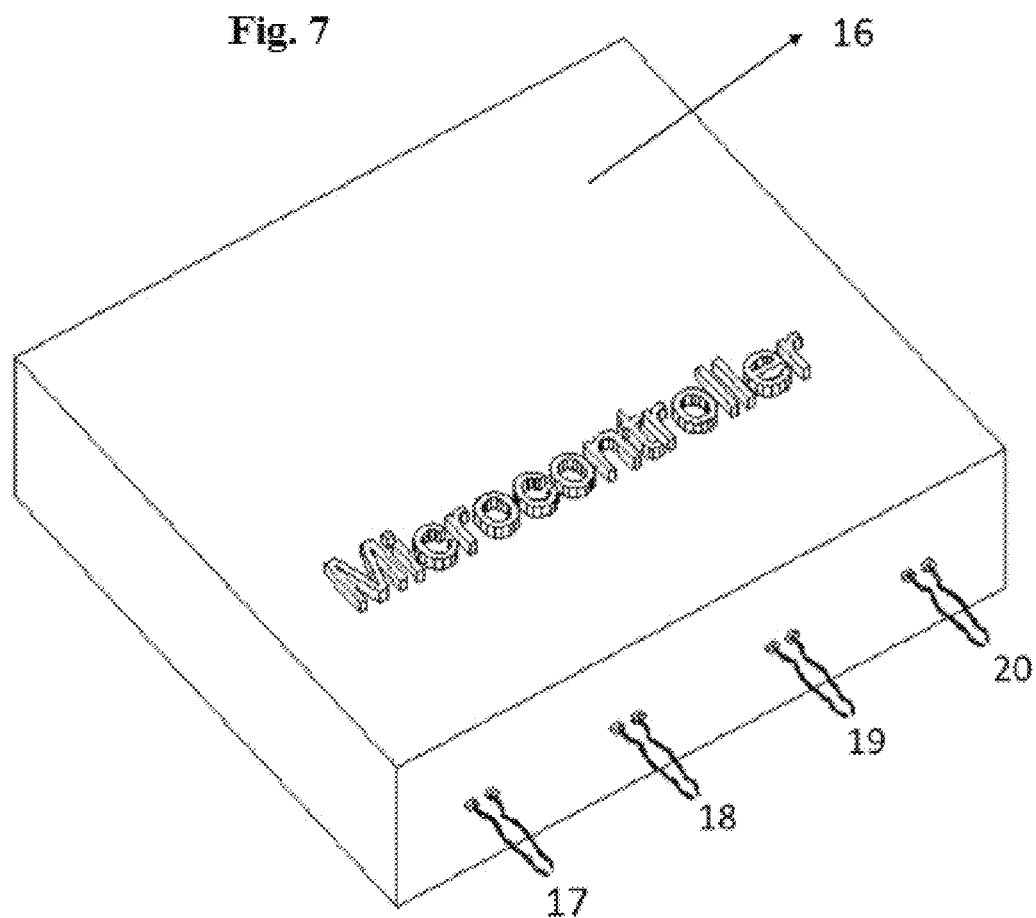
FIG. 7 depicts a microcontroller 16 which can be incorporated into the tissue splitting device as disclosed herein. This embodiment shows a microcontroller with connections or wires to a control 17 for cutting blade motor 11, connections or wires to saw horizontal movement motor 18, connections or wires from the pressure sensor to the microcontroller 19 and wires to a display, such as an LCD display, of pressure parameters 20.

The control of the electronics and electrical devices comes from a microcontroller 16 in FIG. 7 which is interconnected by wire 17 from the microcontroller to control the cutting or sawing motor 11, wire 18 to control horizontal movement motor 12, which controls the movement of the blade through the harvested tissue, cables 19 from the pressure sensor 15 and by wires 20 wires from the microcontroller to the LCD display 4 which conveniently displays the pressure exerted on the tissue sample when the upper compression plate 1A is lowered.

The device as disclosed herein may be made of various materials including metal, hard plastics or polymers, wood, ceramics or combinations thereof.

Terminology.

Terminology used herein is for the purpose of describing particular embodiments only and is not intended to be limiting of the invention.

As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Any numerical range recited herein is intended to include all sub-ranges and values subsumed therein.

Spatially relative terms, such as "under", "below", "lower", "over", "upper", "in front of or" behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees, 180 degrees, or at other orientations) and the spatially relative descriptors used herein interpreted accordingly. Similarly, the terms "upper", "lower", "horizontal space", "height", "upwardly", "downwardly", "vertical", "horizontal" and the like are used herein for the purpose of explanation only unless specifically indicated otherwise. The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A tissue splitting device comprising:
    a clamp comprising an upper plate and lower mounting plate, wherein the upper plate and lower mounting plate are parallel with one another and define a horizontal space between and parallel to the upper plate and lower mounting plate that can accommodate a harvested tissue,
    wherein the clamp comprises an adjustable arm attached to a support base and to the upper plate which is configured to adjust the vertical position of the upper plate thereby adjusting the height of the horizontal space between the upper plate and lower mounting plate,
    wherein the top surface of the upper plate comprises a display operatively connected to one or more pressure sensors on a bottom surface of the upper plate,
    wherein a top surface of the lower mounting plate is a rough, frictioned surface having a surface roughness Ra of at least 1 µm that prevents tissue placed in the clamp from sliding;
    a blade positioned within the space between and parallel the upper plate and lower mounting plate,
    a cutting blade motor operably connected to the blade, and
    a blade movement channel to which one end of the blade is operatively attached, wherein the blade movement channel is longitudinally aligned with the horizontal space between the upper plate and the lower mounting plate and which, during operation of the device, permits forward movement of the blade from one end of the horizontal space to the other end of the horizontal space.

2. The tissue splitting device of claim 1, further comprising a horizontal movement motor that is operatively connected to the blade and can move the blade forward along the blade movement channel.

3. The tissue splitting device of claim 1, further comprising a handle that is operatively connected to the blade and can manually move the blade forward along the blade movement channel.

4. The tissue splitting device of claim 1, further comprising a thickness control which moves the blade upward or downward in the horizontal space between the upper plate and lower mounting plate and a height scale indicator describing the height of the blade.

5. The tissue splitting device of claim 1, wherein the top surface of the bottom plate is a rough surface having a surface roughness $R_a$ greater than 1 µm.

6. The tissue splitting device of claim 1, wherein the bottom surface of the upper plate has a surface roughness, Ra, of greater than 1 µm.

7. The tissue splitting device of claim 1, wherein the surfaces of the upper plate and the lower mounting plate and the blade are sterile.

8. The tissue splitting device of claim 1, wherein the blade has a linear cutting edge and is operatively connected to through the blade movement channel to the cutting blade motor.

9. The tissue splitting device of claim 1, wherein the blade has circular or rotary cutting edge and is operatively connected through the blade movement channel to the cutting blade motor.

10. The tissue splitting device of claim 1, further comprising a microcontroller operatively connected to the adjustable arm and to a pressure sensor so as to control pressure applied to a harvested tissue between the upper and lower mounting plates or control the thickness of a tissue to be split, and, optionally, a display that indicates pressure imposed on a tissue between the upper and lower plates and/or the thickness of the tissue between the upper and lower plates.

11. The tissue splitting device of claim 1, further comprising a microcontroller operatively connected to the cutting blade motor so as to control the speed of the cutting blade and, optionally, connected to a display indicating the speed of the cutting blade.

12. The tissue splitting device of claim 1, further comprising a microcontroller operatively connected to the horizontal movement motor that moves the blade along the blade movement channel so as to control the speed of the blade through the horizontal space between the upper and lower mounting plates, and optionally connected to a display indicating the horizontal speed of the blade.

13. The tissue splitting device of claim 1, further comprising a microcontroller that is operatively connected to the thickness control so as to control the height of the blade and, optionally, connected to a display which indicates the thickness of split tissue produced by splitting tissue between the upper and lower plates.

14. A method for splitting a soft tissue, comprising:
harvesting a tissue sample comprising a soft tissue,
securing the harvested soft tissue between the upper plate and lower mounting plate of the tissue splitting device of claim 1,
setting the blade to a preselected position,
horizontally cutting the secured soft tissue, and
recovering a slice of the soft tissue having a preselected thickness.

15. The method of claim 14, wherein the soft tissue comprises connective tissue.

16. The method of claim 14, wherein the soft tissue comprises keratinized gingival tissue.

17. The method of claim 14, wherein the soft tissue comprises non-keratinized gingival tissue.

18. The method of claim 14, wherein the soft tissue comprises a mucous membrane.

19. A method for performing a soft tissue transplant, comprising:
surgically removing a soft tissue from a subject,
splitting the soft tissue in the tissue splitting device of claim 1 under conditions that provide a layer of viable soft tissue of a uniform thickness, and
transplanting the layer of viable soft tissue into the subject.

20. The method of claim 19, wherein the soft tissue is gingival or connective tissue and wherein the subject is in need of a connective tissue or free gingival tissue graft in the mouth.

* * * * *